(12) United States Patent
Johnson et al.

(10) Patent No.: US 6,338,345 B1
(45) Date of Patent: Jan. 15, 2002

(54) SUBMUCOSAL PROSTHESIS DELIVERY DEVICE

(75) Inventors: George M. Johnson, Santa Ana; Ross Tsukashima; Matthew Thomas Yurek, both of San Diego, all of CA (US)

(73) Assignee: Endonetics, Inc., San Diego, CA (US)

( * ) Notice: Subject to any disclaimer, the term of this patent is extended or adjusted under 35 U.S.C. 154(b) by 0 days.

(21) Appl. No.: 09/524,478

(22) Filed: Mar. 13, 2000

Related U.S. Application Data

(63) Continuation-in-part of application No. 09/287,607, filed on Apr. 7, 1999.

(51) Int. Cl.⁷ .............................................. A61B 19/00
(52) U.S. Cl. ...................................... 128/897; 600/114
(58) Field of Search ......................... 600/29, 101, 104, 600/129, 114; 606/140, 198, 139; 128/897, 898; 604/96

(56) References Cited

U.S. PATENT DOCUMENTS

| | | | |
|---|---|---|---|
| 3,094,122 A | 6/1963 | Gauthier et al. | |
| 3,204,634 A | 9/1965 | Koehn | |
| 4,183,102 A | 1/1980 | Guiset | |
| 4,351,333 A | 9/1982 | Lazarus et al. | |
| 4,439,872 A | 4/1984 | Henley-Cohn et al. | |
| 4,631,188 A | 12/1986 | Stoy et al. | |
| 4,636,213 A | 1/1987 | Pakiam | |
| 4,740,208 A | 4/1988 | Cavon | |
| 4,820,303 A | 4/1989 | Brauman | |
| 4,943,618 A | 7/1990 | Stoy et al. | |
| 4,955,907 A | 9/1990 | Ledergerber | |
| 4,963,150 A | 10/1990 | Brauman | |
| 5,002,583 A | 3/1991 | Pitaru et al. | |
| 5,252,692 A | 10/1993 | Lovy et al. | |
| 5,301,682 A | 4/1994 | Debbas | |
| 5,336,263 A | 8/1994 | Ersek et al. | |
| 5,554,185 A | 9/1996 | Block et al. | |
| 5,580,568 A | 12/1996 | Greff et al. | |
| 5,624,453 A * | 4/1997 | Ahmed | 606/140 |
| 5,658,330 A | 8/1997 | Carlisle et al. | |
| 5,667,767 A | 9/1997 | Greff et al. | |
| 5,667,778 A | 9/1997 | Atala | |
| 5,695,480 A | 12/1997 | Evans et al. | |
| 5,697,969 A | 12/1997 | Schmitt et al. | |
| 5,702,361 A | 12/1997 | Evans et al. | |
| 5,755,658 A | 5/1998 | Wallace et al. | |
| 5,779,734 A | 7/1998 | Ledergerber | |
| 5,785,642 A | 7/1998 | Wallace et al. | |
| 5,823,198 A | 10/1998 | Jones et al. | |
| 5,824,063 A | 10/1998 | Cox | |
| 5,830,178 A | 11/1998 | Jones et al. | |
| 5,861,036 A | 1/1999 | Godin | |
| 5,885,619 A | 3/1999 | Patel et al. | |
| 5,910,105 A * | 6/1999 | Swain et al. | 600/114 |
| 6,231,613 B1 | 5/2001 | Greff et al. | |
| 6,234,955 B1 | 5/2001 | Silverman et al. | |
| 6,238,335 B1 * | 5/2001 | Silverman et al. | 600/29 |
| 6,251,063 B1 | 6/2001 | Silverman et al. | |
| 6,251,064 B1 | 6/2001 | Silverman et al. | |

FOREIGN PATENT DOCUMENTS

| | | |
|---|---|---|
| EP | 0 628 292 A1 | 12/1994 |
| SU | 1655469 A1 | 6/1991 |
| WO | WO 00/33908 | 6/2000 |

* cited by examiner

*Primary Examiner*—John P. Lacyk
*Assistant Examiner*—Brian Szmal
(74) *Attorney, Agent, or Firm*—Knobbe, Martens, Olson, & Bear, LLP

(57) ABSTRACT

Disclosed is a delivery device for controllably delivering a prosthetic bulking device below a tissue surface such as below the mucosa to treat gastroesophageal reflux disease. The delivery device may be embodied in a deployment catheter, an endoscope, or an endoscope attachment. The bulking device cooperates with residual lower esophageal sphincter (LES) function to increase LES closing pressure. Methods are also disclosed.

39 Claims, 11 Drawing Sheets

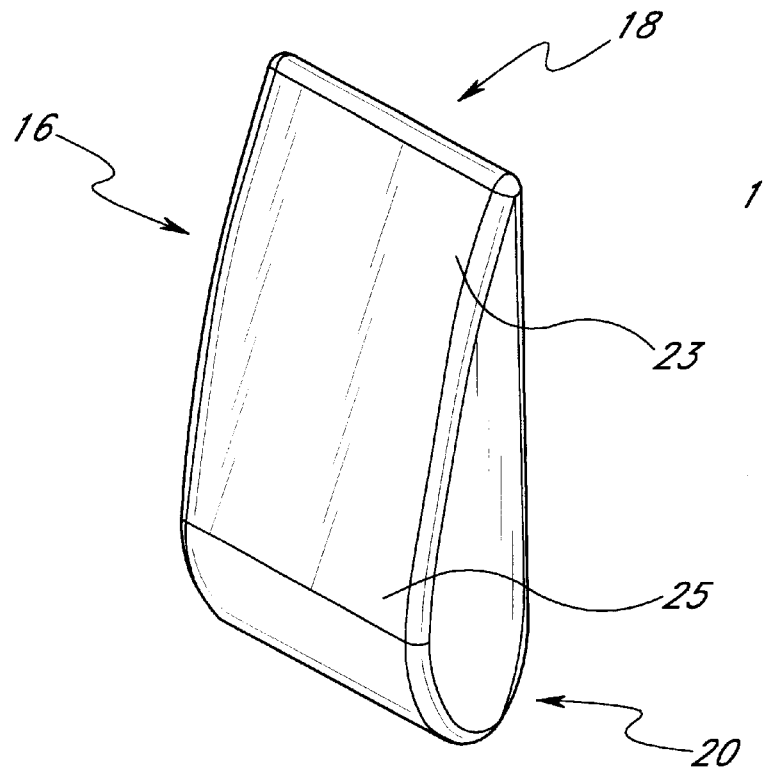
FIG.3
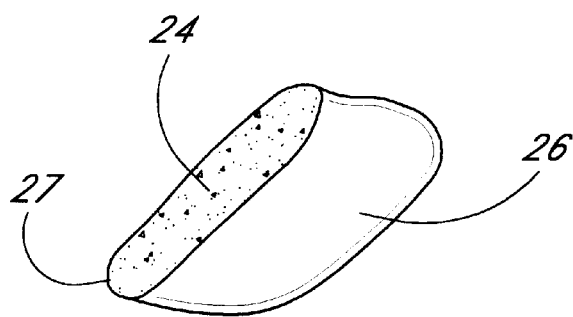
FIG.5
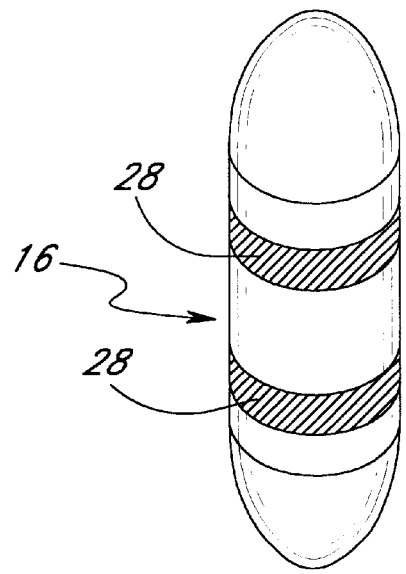
FIG.4
FIG.6

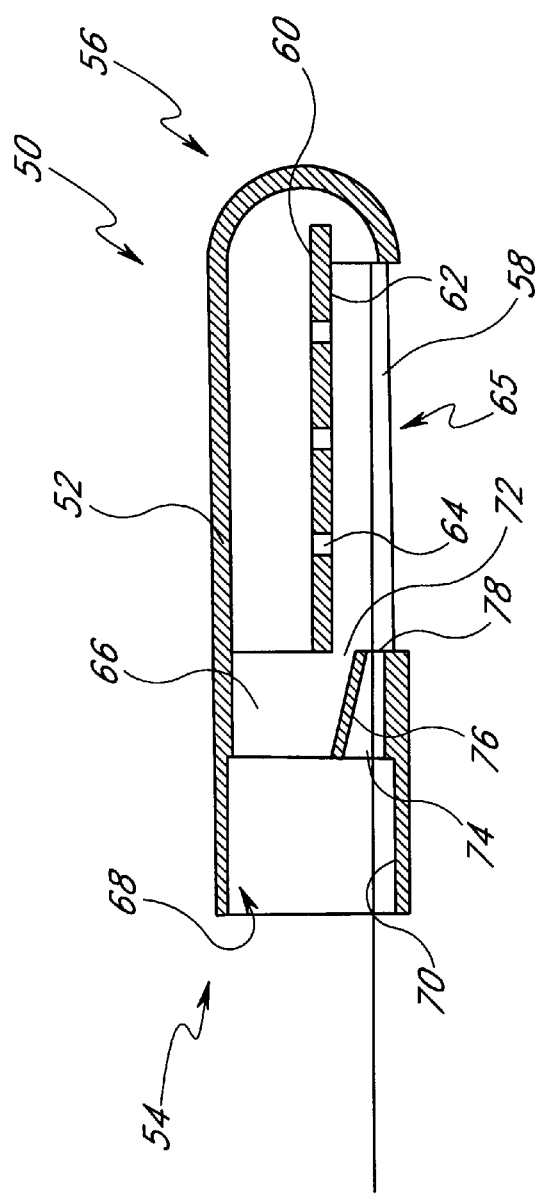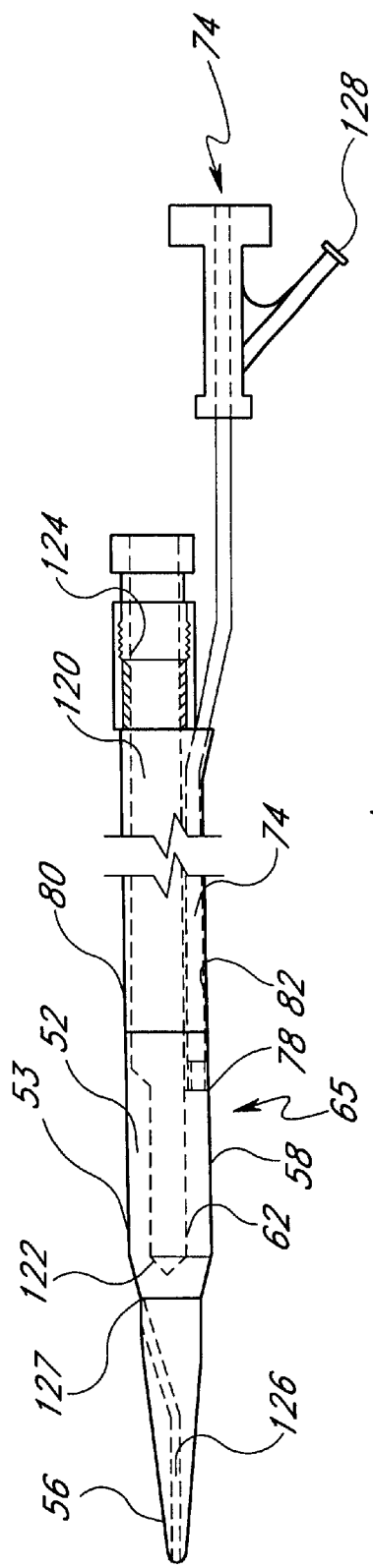

SUBMUCOSAL PROSTHESIS DELIVERY DEVICE

The present application is a continuation-in-part of pending application Ser. No. 09/287,607 filed on Apr. 7, 1999, entitled Submucosal Esophageal Bulking Device.

FIELD OF THE INVENTION

The present invention relates generally to the field of esophageal prosthetics. More specifically, a prosthesis delivery device is disclosed for submucosal insertion of a prosthetic bulking device.

BACKGROUND OF THE INVENTION

Gastroesophageal reflux is a physical condition in which stomach acids reflux, or flow back from the stomach into the esophagus. Frequent reflux episodes (two or more times per week), may result in a more severe problem known as gastroesophageal reflux disease (GERD). Gastroesophageal reflux disease is the most common form of dyspepsia, being present in approximately 40% of adults in the United States on an intermittent basis and some 10% on a daily basis.

Dyspepsia, or heartburn, is defined as a burning sensation or discomfort behind the breastbone or sternum and is the most common symptom of GERD. Other symptoms of GERD include dysphasia, odynophagia, hemorrhage, water brash, and pulmonary manifestations such as asthma, coughing or intermittent wheezing due to acid aspiration. Dyspepsia may also mimic the symptoms of a myocardial infarction or severe angina pectoris. Many factors are believed to contribute to the onset of GERD including transient lower esophageal sphincter relaxations, decreased LES resting tone, delayed stomach emptying, and an ineffective esophageal clearance. Many in the field agree, however, that the primary cause of GERD is the lack of competency of the lower esophageal sphincter.

The lower esophageal sphincter, or valve, is comprised of smooth muscle located at the gastroesophageal (GE) junction and functions to allow food and liquid to pass into the stomach but prevent regurgitation of stomach contents. At rest, the LES maintains a high-pressure zone between 10 and 30 mm Hg above intragastric pressure. Upon deglutition, the LES relaxes before the esophagus contracts, allowing food to pass through into the stomach. After food passes into the stomach, the LES contracts to prevent the stomach contents and acids from regurgitating into the esophagus. The mechanism of LES opening and closing is influenced by innervation via the vagus nerve and hormonal control of gastrin and possibly other gastrointestinal hormones.

The severity of GERD varies from patient to patient and in extreme cases complications including esophageal erosion, esophageal ulcers, and esophageal stricture are observed. Esophageal stricture is a serious condition which results from prolonged exposure of the esophageal mucosa to acid reflux. The most common clinical manifestation of stricture is dysphasia. Unlike dysphasia from non-strictured esophageal reflux, dysphasia caused by stricture is progressive in that the size of a bolus which can pass into the stomach progressively becomes smaller. In addition to esophageal erosion and ulceration, prolonged exposure of the esophageal mucosa to stomach acid can lead to a condition known as Barrett's Esophagus. Barrett's Esophagus is an esophageal disorder that is characterized by the replacement of normal squamous epithelium with abnormal columner epithelium. This change in tissue structure is clinically important not only as an indication of severe reflux, but the appearance of columner epithelium in the esophagus is indicative of cancer.

Current methods to treat gastroesophageal reflux disease consist of lifestyle changes such as weight loss, avoidance of certain foods that exacerbate the symptoms of GERD and avoidance of excessive bending. Elevation of the head of the bed helps prevent nocturnal reflux. While these avoidance strategies may be helpful, there is relatively little data supporting the efficacy of lifestyle modification alone for the treatment of GERD.

Medications for the treatment of GERD have been administered for years with little or no success. Conventional antacids, such as TUMS® and ROLAIDS®, produce short-term relief, but often have side effects including diarrhea and constipation. H2 receptor antagonists, such as Cimetidine and Ranitidine, are relatively more effective in controlling GERD symptoms but these symptomatic therapies fail to treat the underlying cause of the disease. More powerful secretory inhibitors, such as the proton pump inhibitors Omeprazole and Lansoprazole are more effective than the H2 antagonists but these drugs are expensive and, in the long term, produce negative side effects.

Surgery has become an attractive alternative for the treatment of GERD when lifestyle modification and medications fail to treat this debilitating condition. There are numerous reflux operations available which perhaps reflect the inadequacy of any one procedure to totally control the problem. The most commonly performed operation, Nissen Fundoplication, has been effective, but is often complicated by stricture formation or gas bloat syndrome. A laparoscopic Nissen procedure has also been developed, adding another dimension of difficulty, and long-term results remain questionable. In addition, a percutaneous laparoscopic technique has been developed. (See, for example, U.S. Pat. No. 5,006, 106 to Angelchik). Minimally invasive techniques, such as transesophageal implantation of a prosthetic valve have also been attempted. (See, for example, U.S. Pat. No. 4,846,836 to Reich). Despite extensive attempts in the field to treat and prevent GERD, existing forms of treatment all have shortcomings.

In view of the foregoing, and notwithstanding the various efforts exemplified in the prior art, there remains a need for a minimally invasive bulking prosthesis and deployment methodology for transesophageal delivery into the vicinity of the lower esophageal sphincter.

SUMMARY OF THE INVENTION

In accordance with one aspect of the present invention, there is provided an overtube for coupling to the distal end of an endoscope to produce a submucosal prosthesis delivery device. The overtube comprises an elongate flexible tubular body, having a proximal end, a distal end and a longitudinal axis. At least one lumen extends into the tubular body, for receiving an endoscope. An opening is provided on the body, in communication with the lumen, and a limit surface is provided within the body, aligned with the opening to limit the depth to which tissue can enter the opening. Typically, the tubular body is defined by a sidewall and the opening is in the sidewall. The limit surface in one embodiment lies on a first plane which is offset from the sidewall and preferably is substantially parallel to the longitudinal axis. The limit surface is preferably provided with a plurality of apertures, to permit vacuum from the endoscope to draw tissue through the opening in the direction of the limit surface.

In accordance with another aspect of the present invention, there is provided a method of introducing a flowable media into a predetermined shape beneath a tissue layer. The method comprises the steps of identifying a first site on a tissue surface, and lifting tissue a predetermined distance away from the plane of the surface to create a low pressure zone beneath the tissue. A first volume of flowable media is injected into the low pressure zone so that the media takes on a shape which is influenced by the low pressure zone. The media is thereafter permitted to harden sufficiently to substantially retain the shape.

In one embodiment, the identifying a site on a tissue surface step comprises identifying a site on the wall of the esophagus. The site is preferably in the vicinity of the lower esophageal sphincter. The method may further comprise the steps of identifying a second site and introducing a second volume of flowable media into the second site, thereafter permitting the second volume of media to harden sufficiently to substantially retain the shape. At least one of the first and second site are preferably on the posterior wall of the esophagus.

In accordance with a further aspect of the present invention, there is provided a method of stabilizing a tissue site and introducing a prosthesis beneath the tissue. The method comprises the steps of providing an elongate flexible tubular device, having a side opening near a distal end thereof. The side opening is positioned at the site, and suction is applied to the device to draw tissue laterally into the side opening. Lateral advance of the tissue is limited by contacting the tissue with a limiting surface within the device. A prosthesis is thereafter introduced beneath the surface at the site while the tissue is in contact with the limiting surface.

In accordance with a further aspect of the present invention, there is provided a method of introducing a prosthesis beneath a tissue surface. The method comprises the steps of providing a prosthesis delivery device having an elongate body with a proximal end and a distal end, a concavity near the distal end, and an inner introduction lumen having a distal opening directed across the concavity. The concavity is positioned adjacent a site on a tissue surface, and tissue is drawn into the cavity. The prosthesis is advanced out of the distal end of the inner introduction lumen and through the tissue surface.

In accordance with a further aspect of the present invention, there is provided a delivery device for introducing a prosthesis beneath a tissue surface. The delivery device comprises an elongate body, having a proximal end and a distal end. A tissue stabilizing surface is provided on the body, and a prosthesis deployment lumen extends through the body, the deployment lumen having a longitudinal axis and a distal end. The distal end of the deployment lumen is positioned proximally of the tissue stabilizing surface. Preferably, the tissue stabilizing surface comprises a concave surface. The delivery device preferably comprises a lumen extending through the body and communicating with the tissue stabilizing surface, so that suction may be applied to the lumen to draw tissue adjacent the tissue stabilizing surface.

In accordance with another aspect of the present invention, there is provided a delivery system for delivering an expandable submucosal bulking agent. The delivery system comprises an elongate flexible body, having a proximal end, a distal end, and a tissue stabilizer near the distal end. A tubular cannula, having a sharpened distal end, is positioned within the body. The cannula is axially movable such that the sharpened distal end can penetrate tissue stabilized by the stabilizer. A plunger is movably positioned within the cannula, for ejecting bulking agent prepositioned within the cannula. In one embodiment, the plunger is distally advanceable beyond the distal end of the sharpened tip. Preferably, the tissue stabilizer comprises a cavity on a side of the flexible body. The tubular body comprises a lumen in communication with the cavity for applying vacuum to the cavity to draw tissue therein.

Further features and advantages of the present invention will become apparent to those of skill in the art in view of the detailed description of preferred embodiments which follows, when considered together with the attached drawings and claims.

BRIEF DESCRIPTION OF THE DRAWINGS

FIG. 3 is a perspective schematic view of an esophageal bulking device of the present invention.

FIG. 4 is a perspective schematic view of another esophageal bulking device of the present invention.

FIG. 5 is a cross-sectional perspective view of an esophageal bulking device of the present invention.

FIG. 6 illustrates an embodiment of an esophageal bulking device of the present invention having surface regions which promote tissue ingrowth.

FIG. 16 is a side elevational cross-section through a cap for attachment to an endoscope to deliver a submucosal prosthesis.

FIG. 17 is a side elevational schematic view of an overtube in accordance with the present invention, for receiving an endoscope to deliver a submucosal prosthesis.

DETAILED DESCRIPTION OF THE PREFERRED EMBODIMENT

Figure 1:
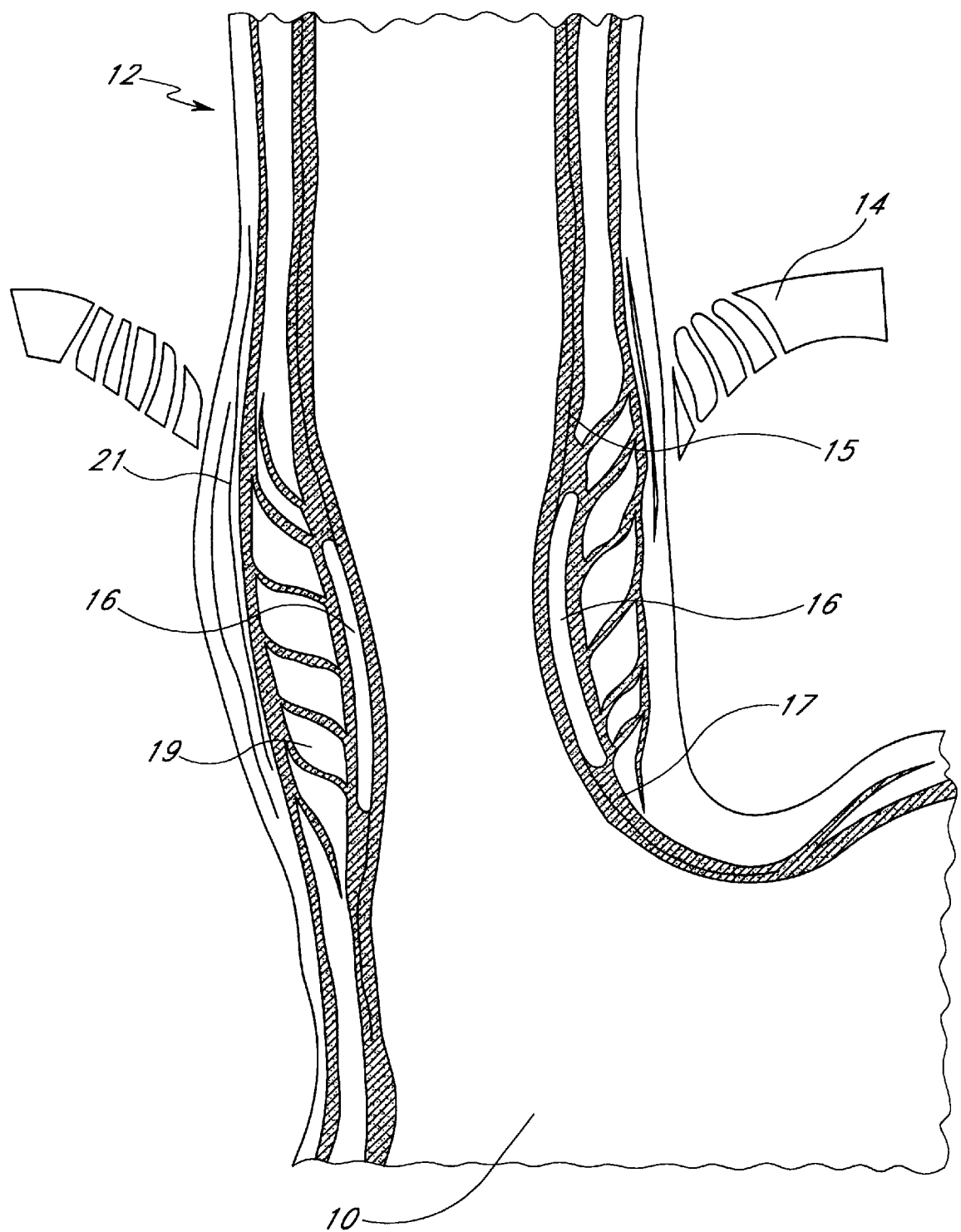
FIG. 1 is a schematic view of a pair of gastroesophageal bulking prostheses in accordance with the present invention, positioned at about the junction between the esophagus and the stomach, before expansion, in which the LES is in an open configuration.

Referring to FIG. 1, there is illustrated a schematic representation of the stomach 10 and a portion of the lower esophagus 12. The esophagus 12 extends through the diaphragm 14, below which the esophagus 12 communicates with the interior of the stomach 10. A pair of gastroesophageal prosthetic bulking devices 16, in accordance with the present invention, is illustrated at about the junction between the lower esophagus 12 and the stomach 10.

In the illustrated embodiment, the bulking device 16 is delivered in the submucosa 17. The submucosa 17 is a fibrous layer of tissue positioned between the mucosa 15 and a layer of circular muscle 19. The circular muscle 19 is surrounded by a layer of longitudinal muscle 21, as is well understood in the art. The bulking device 16 is preferably delivered beneath the mucosa 15 as is discussed elsewhere herein. The bulking device 16 may either be delivered within the submucosa 17 as illustrated, or at the interface of adjacent tissue planes, such as between the mucosa 15 and submucosa 17, or between the submucosa 17 and circular muscle 19. Preferably, the bulking device 16 is positioned radially inwardly from the circular muscle layer 19.

Although the anatomy illustrated in FIG. 1 is generally normal, except for the improperly functioning native lower esophageal sphincter, the present invention is also useful in patients having lower esophageal abnormalities, such as hiatal hernia. In this condition, a portion of the wall of the stomach 10 extends upwardly through the diaphragm 14 and herniates superiorly to the diaphragm 14. The existence of a hiatal hernia or another abnormality in the lower esophagus may affect the delivered position of the esophageal prosthetic bulking device 16, but may not disqualify a patient otherwise treatable with the prosthetic bulking device 16 of the present invention.

As illustrated in FIG. 1, the esophageal bulking device 16 is generally delivered below the mucosa such as in the submucosa or between adjacent tissue planes in the vicinity of the sphincter. The submucosa is a springy tissue, which needs to be expanded in order to produce a cavity for delivery of the bulking device 16. Alternatively, the submucosa can be cut using mechanical cutting techniques or cautery tools as is discussed in more detail below.

Ideally, the esophageal bulking device 16 is delivered in a position that extends across or is closely adjacent to the sphincter so that residual sphincter activity is optimized and the mucosal regions of the esophagus are protected from acid reflux. The precise positioning of the prosthesis 16 depends largely on the patient's anatomy and the severity of GERD, and will be a matter of clinical choice at the time of delivery. In patients with a hiatal hernia, for example, the esophageal bulking device 16 is delivered as close as possible to the sphincter but care must be taken to insure that the hernia will not perturb the operation of the bulking device 16.

Figure 2:
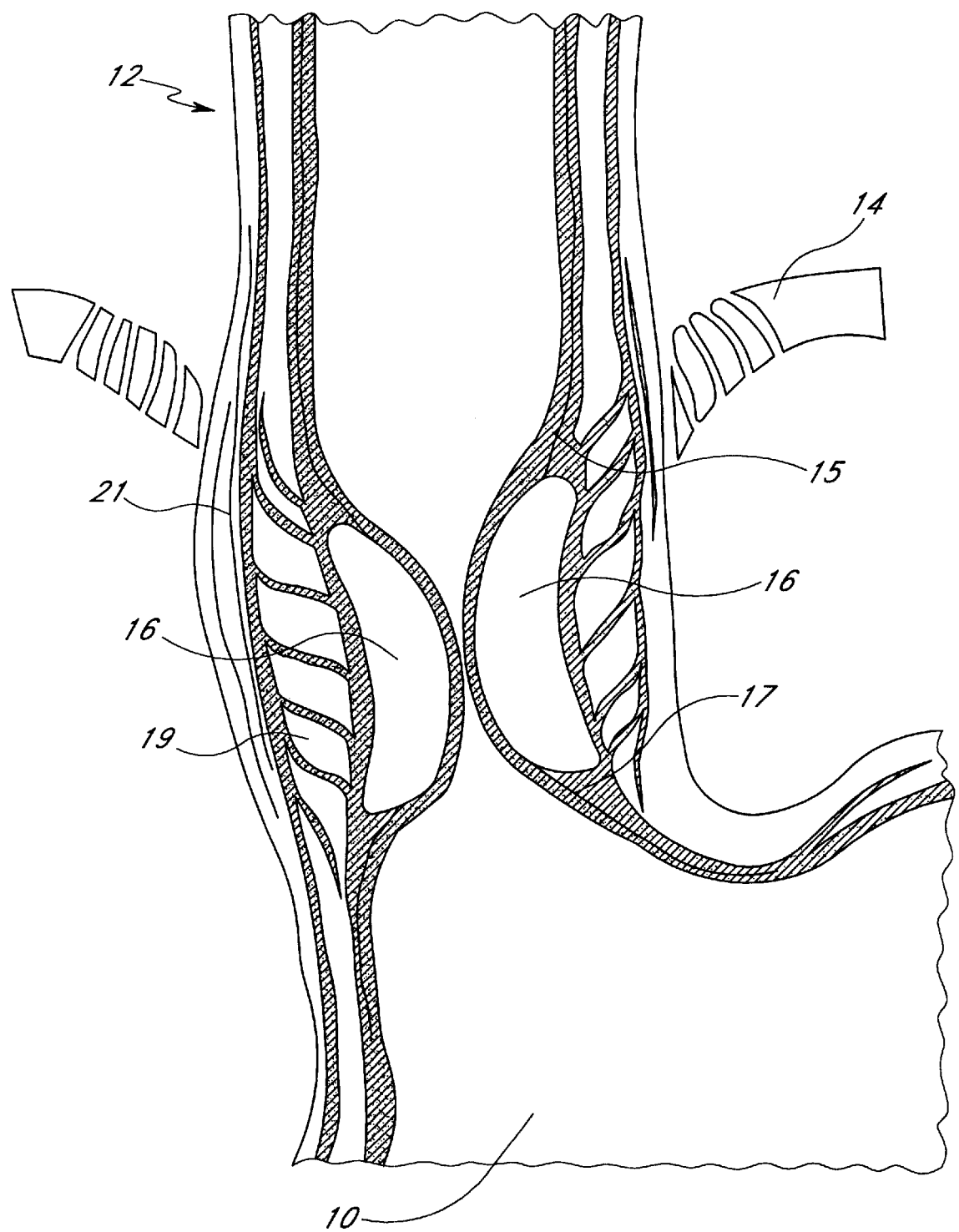
FIG. 2 is a schematic view as in FIG. 1, following expansion of the prostheses, in which the LES is illustrated in a closed configuration.

Advantageously, the esophageal bulking device 16 of the present invention enhances any residual closing pressure function of the sphincter so as to effectively reduce or prevent the reflux of stomach contents into the esophagus. In an open or relaxed state, as shown in FIG. 1, the esophageal bulking device allows food and liquid to pass through the esophagus into the stomach. However, when the sphincter is closed, as shown in FIG. 2, the esophageal bulking device increases the closing pressure along a sufficient axial length that, in cooperation with the contraction of the sphincter, it inhibits or prevents the reflux of stomach contents.

Depending on the degree of LES dysfunction, more than one esophageal bulking device 16 can be delivered into the lining of the esophagus. Where two or three or more esophageal bulking devices 16 are utilized to improve LES function, the bulking devices 16 may be spaced around the circumference of the LES. Generally, multiple bulking devices 16 will be located substantially in the same transverse plane perpendicular to the longitudinal axis of the esophagus. Use of multiple bulking devices 16 without rigid interconnection permits the LES to radially expand to a greater degree so as to permit bolus passage and better accommodate the natural function of the esophagus.

Depending on the patient's anatomy and the extent of GERD, esophageal bulking devices 16 having various lengths and cross sectional profiles are delivered so as to maximize operation with the residual LES function. Using common esophageal manometry and endoscopic techniques, for example, medical personnel can measure the degree of closure (e.g., closing pressure) achieved by the sphincter as well as any unique anatomical features of the lower esophagus for a particular patient when selecting specific shapes and designs of esophageal bulking devices 16 to be delivered.

Due to the irregular cross-sectional configuration of the closed sphincter, the cross-sectional configuration of the bulking device 16 can take on any of a wide variety of shapes including, but not limited to, those specific embodiments disclosed herein. In general, the desired expanded transverse plane thickness of the esophageal bulking device 16 will depend on the lumen diameter and the extent of LES dysfunction. Devices 16 produced in accordance with the present invention can be rated according to their bulking area, which represents the total cross-sectional area the device will occupy within the region at or about to the sphincter, referred to as the "bulking zone". In general, a larger transverse cross-sectional area will produce a higher closing pressure for a given state of the disease.

FIGS. 3, 4, 5 and 6 illustrate different configurations and features of the esophageal bulking device 16 of the present invention. The esophageal bulking device 16 generally comprises an oblong, cylindrical, elliptical, toric or pillow shape and has a proximal end 18 and a distal end 20. As used herein, "distal" shall refer to a location closer to the stomach and "proximal" shall refer to a location closer to the mouth. In one embodiment, a proximal portion 23 has a smaller cross-sectional area than a distal portion 25. Alternatively, embodiments of the esophageal bulking device 16 can be a cylindrical shape (FIGS. 4 and 6) or elliptical shape (not illustrated) wherein a proximal portion 23 and a distal portion 25 have roughly the same cross-sectional area and shape. The bulking device 16 preferably substantially retains its pre-implanted configuration once delivered into the body.

Suitable esophageal bulking devices 16 comprise a soft, flexible body that may have an expanded axial length from 0.5 cm to 5.0 cm, a width (circumferential direction) of 0.2 cm to 2.0 cm, and a thickness (radial direction) of 0.2 cm to 2.0 cm. Many esophageal bulking devices 16 of the present invention have a length within the range of 1.0 cm to 4.0 cm, a width within the range of 0.2 cm to 1.5 cm, and a thickness within the range of 0.2 cm to 1.5 cm. In one embodiment, the esophageal bulking device 16 has a length of 2.0 cm to 3.0 cm, a width of 0.8 cm to 1.0 cm, and a thickness of 0.4 cm to 0.6 cm. The cross-sectional configuration may be circular, oval or other configuration, as desired.

Length to thickness ratios are generally no more than about 15:1 and are often no more than about 6:1 or 4:1. Length to thickness ratios on the order of less than 3:1 may also be desirable depending upon the severity of the condition. The cross-sectional area of the bulking device 16 may also vary at different points along the length of the same device 16. As mentioned above, optimal dimensions may be patient specific and can be determined through routine experimentation of one of skill in the art in view of the disclosure herein.

An LES having a relaxed open diameter of 2.0 cm, for example, has a cross sectional lumen area of 3.14 $cm^2$. A 25% bulking function could be accomplished by providing a bulking device 16 having a total cross-sectional area in the bulking zone of about 0.785 $cm^2$. The bulking area may represent the area of an esophageal bulking device 16 having a generally oval or rectangular cross-section (e.g., 0.443 cm×1.772 cm) which is adapted to extend axially for a length of 1 to 3 cm beneath the mucosa.

In general, the objective of the present invention is to increase the closing pressure of the lower esophageal sphincter. The present inventors believe that a closing pressure of at least a certain minimum closing threshold value, maintained along a minimum axial effective LES length will satisfactorily reduce esophageal reflux. In the intra-abdominal (i.e., inferior to the diaphragm 14) esophagus, about 2 cm of effective LES length appears desirable. An average pressure along that length is preferably in excess of about 10 mm Hg, preferably at least about 15 mm Hg, and optimally in the range of from about 15 mm to about 30 mm Hg.

Within certain outer limits, any increase in the closing pressure in the LES may improve symptoms. For example, some patients have an LES closing pressure on the order of about 5 mm Hg, which is accompanied by severe GERD symptoms. At the high end, a closing pressure in excess of about the minimum diastolic pressure inhibits blood flow, thereby increasing the risk of localized pressure necrosis. Pressure slightly below the minimal diastolic pressure may still interfere with swallowing function. The present invention therefore preferably enables increasing the closure pressure from a pretreatment value below about 10 to 15 mm Hg to a post treatment value of preferably on the order of from about 18 or 20 to about 25 or 30, along a length of at least about 1.0 cm and preferably at least about 2 cm or 2.5 cm or more.

Once the total desired cross-sectional area and length of the bulking device is determined for a particular patient or class of patients, the allocation of that cross-sectional area to a single bulking device or a series of bulking devices which together produce the desired cross-sectional area must be determined. This clinical decision will take into account any unique aspects to the patient's lower esophageal anatomy, together with the extent of the disease and consequent total area of bulking required. In general, a larger single bulking device will require a larger submucosal pocket for delivery and the consequent greater disruption of tissue in the immediate area of the prosthesis, which may be undesirable in some patients. In addition, a larger single device may have a greater likelihood of migration which would be reduced if the same total prosthesis volume was delivered in two bulking devices each having half the cross-sectional area of the single larger device.

The bulking device 16 is preferably flexible and has a high degree of softness which approaches that of the native mucosal tissue, to minimize trauma to the adjacent tissue. The material of the bulking device 16 is thus preferably soft enough so that is incapable of exerting sufficient localized pressure to cause pressure necrosis. A localized pressure in excess of about 70 mm Hg gives rise to a risk of localized tissue necrosis. As will be understood by those of skill in the art, the configuration of the bulking device 16 (e.g. sharp edges, etc.) operates in cooperation with the softness of the construction materials to optimize the compatibility of the bulking device. A smooth, blunt a traumatic outer surface is preferred.

One suitable bulking device construction comprises the use of an inflatable pillow or balloon, partially or completely filled with a liquid or semi-liquid, which allows one end to be compressed by peristaltic compression and the other end to expand bulbously. The ability of the volume of the bulking device to flow from one end of the bulking device to the other and back permits the passage of a peristaltic wave, as will be appreciated by those of skill in the art in view of the disclosure herein. Suitable elastomeric balloons comprise material such as silicone, latex, urethane, and others as will be understood by those of skill in the art.

In addition to being soft, the bulking device in some embodiments may also be compressible. This enables the filler 24 and body of bulking device 16 to expand when nothing is passing through the LES, but compress, for example, to no more than about 4 mm and preferably no more than about 2 mm in radial thickness during swallowing. After swallowing, the filling material 24 and body will desirably rebound back to facilitate the LES closure function. In this manner, the bulking device 16 can cooperate with any residual function of the LES to minimize the occurrence of reflux.

Referring to FIG. 5, the bulking device 16 generally comprises an outer surface 26 which encloses a filler 24 therein. The outer surface 26 may be homogeneous with the filler 24, or may be the surface of a dissimilar material in the form of a flexible wall 27 to encapsulate the filler. A homogeneous material outer wall 27 may be provided with a different physical property than the filler 24, such as by heat treatment, solvent exposure or the like to provide a barrier coating around the filler 24.

The esophageal bulking device 16 can be manufactured as a unitary or multi-component structure in a variety of ways as will be appreciated by those of skill in the art in view of the disclosure herein. The bulking device 16, for example, may be a unitary structure molded as a single piece of biocompatible foam material such as silicone foam or polyurethane foam, or may be cut from a block of such foam. Such foam parts can be made with an outer skin 26 of porous foam that facilitates tissue ingrowth.

Alternatively, the esophageal bulking device 16 can comprise a body having at least two components connected together and can be made, for example, by positioning an outer sleeve or layer 27 of porous material such as expanded polytetrafluoroethylene (PTFE) or other tissue ingrowth material around the filler 24 by either a simple filling operation or by bonding the two materials together. If expanded PTFE is used, a PTFE surface etching step prior to bonding with a silicone based glue may be performed.

Alternatively, a process of gluing by simultaneously compressing and heating a stack-up of foam, glue and PTFE can be employed. The outer layer 27 may be secured to the bulking device 16 in any of a variety of manners, such as by solvent bonding, thermal bonding, adhesives, and others as will be apparent to those of skill in the art in view of the disclosure herein.

The present inventors further contemplate embodiments of the esophageal bulking device 16 which have surface textures, coatings or structures to resist migration. In general, the entire outer surface 26 of the outer layer 27 or filler 24 can be coated or textured to facilitate tissue attachment such as by cellular ingrowth. The resulting attachment surface 26 can be integral with the bulking device 16 or can be directly or indirectly connected to the bulking device 16 so that the device 16 can be positioned and retained in the desired position within the esophageal wall. The outer surface 26 may additionally, or alternatively, be provided with any of a variety of tissue retention structures such as hooks, barbs, tacks, clips, sutures, staples, tissue adhesives, attachment strips, attachment spots, attachment connectors, or other attachment means which will be understood by those of skill in the art in view of the disclosure herein.

As illustrated in FIG. 6, one embodiment of the present invention is alternatively provided with one or more attachment surfaces 28 spaced about the device 16 so as to facilitate tissue ingrowth from the adjacent tissue over less than the entire surface 26 of the implant. The design, spacing and total surface area of the attachment surfaces 28 can be varied widely, depending upon the clinical objective.

For example, in an embodiment in which removal is not anticipated, the tissue ingrowth surface area can be as high as 75% to 100% of the surface 26 of the bulking device 16. Alternatively, in an application where the bulking device 16 is preferably removable after a period of time, the percentage of cellular ingrowth surface is preferably kept to the minimum required to reasonably resist migration within the esophageal wall. Thus, in some embodiments, the tissue ingrowth surface 28 covers no more than about 20% and possibly no more than about 5% of the total surface area of the bulking device 16. In this manner, trauma to the tissue upon removal of the bulking device 16 can be minimized. The ease of removal of the bulking device 16 may be desirable because new implants which better accommodate the changing anatomy of the patient during the progression of the patient's LES disfunction and/or age may be indicated.

In one embodiment, one or more attachment zones 28 may extend circumferentially around the bulking device 16. Alternatively, the tissue ingrowth surfaces 28 may extend axially along the length of the esophageal bulking device 16. Further, the attachment zones 28 can be provided in the form of spots or patches distributed around the surface of the esophageal bulking device 16.

The porosity of the cellular ingrowth regions 28 may range from about 20 µm to about 100.0 µm or greater. Desirably, the porosity of the cellular ingrowth regions 28 ranges from 20 µm to 50 µm and, in many embodiments, the porosity of the cellular ingrowth regions 28 ranges from 20 µm to 30 µm.

Suitable outer layer 27 and/or attachment surface 28 materials include polytetrafluoroethylene (PTFE), polyethylene terephthalate, polyester, polyurethane, silicone, Dacron, polypropylene knit, and other materials which will be apparent to those of skill in the art in view of the present disclosure. In one embodiment of the invention, the cellular ingrowth region 28 comprises PTFE having a 22 µm pore size. This porosity appears to permit shallow ingrowth into the esophageal bulking device 16 to prevent axial migration of the device 16 along tissue planes yet allows for relatively easy explant.

Delivery of the esophageal bulking device 16 below the mucosa can be accomplished in any of a variety of ways, as will be apparent to those of skill in the art in view of the disclosure herein. Delivery systems can be specially constructed or assembled from existing endoscopic and other surgical tools to accomplish the basic delivery steps.

In general, the delivery site for a particular patient is identified, such as by endoscopy and manometry. Tissue adjacent to the delivery site is preferably immobilized to permit a puncture or incision to be made. Immobilization of the esophageal lining may be accomplished by grasping the tissue utilizing forceps, such as those which may be advanced through a working channel on an endoscope. Alternatively, a vacuum may be applied to a lumen through an endoscope to immobilize the tissue.

Using counter-traction on the tissue applied by way of the tissue grasper or vacuum, the mucosa is pierced to enable insertion of the prosthesis. The mucosal layer may be pierced in a variety of ways, as will be recognized in the art. In accordance with one aspect of the present method, a needle is utilized to pierce the mucosa and create a blister by injecting a volume of fluid such as saline solution. Alternatively, an electrocautery cutter or any of a variety of sharp dissection tools may be utilized to pierce the mucosa and provide access to the submucosal area.

Once an aperture has been formed in the mucosa, a pouch is formed in the submucosa. The pouch may be formed by liquid infusion to enlarge the blister discussed above. Alternatively, any of a variety of blunt tools may be utilized to achieve a blunt dissection in the submucosa or between adjacent tissue planes to form a pouch for receiving the prosthesis. Alternatively, an inflation device, such as a balloon, may be specially shaped for insertion and inflation to separate submucosal tissue and provide a submucosal pouch.

Following formation of a submucosal pouch, one or more bulking devices 16 are introduced therein. The bulking device 16 may be inserted by way of a grasper, clamshell deployment device, or other tools. Depending upon the shape and compliancy of the bulking device 16, the bulking device 16 may be deployed from the distal end of a tubular element, such as by advancing an axially moveable core to push the prosthesis from the distal end of the tube. One or more pull elements such as wires, strings or tabs may be provided on the bulking device 16, so that a distally extending pull element may be advanced into the pouch under distal force using a grasper, or a second mucosal puncture inferior to the primary mucosal puncture may be provided through which to pull a pull element, thereby advancing the bulking device 16 inferiorly into the pouch.

Following placement of the bulking device 16 into the submucosal pouch, the mucosal opening closes naturally or can be closed using any of a variety of closure techniques. A conventional suture, ligating bands or staples or other clips, may be utilized endoscopically, as will be understood in the art. Alternatively, a topical glue or other adhesive patch may be utilized to close the opening in the mucosa.

Figure 7:
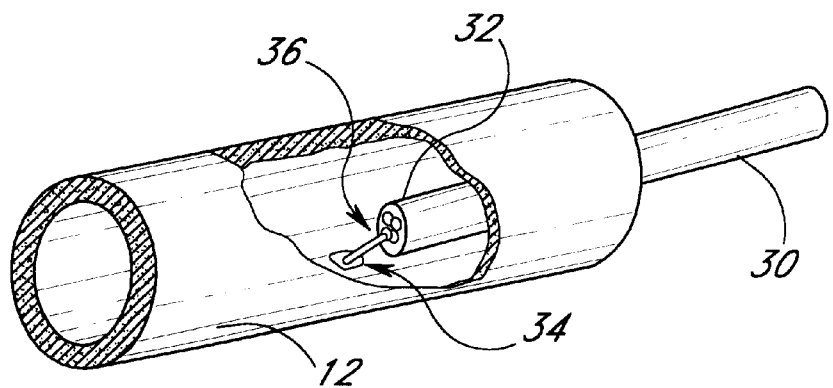
FIG. 7 is a fragmentary perspective view of an endoscope positioned within the esophagus prior to formation of a blister or pocket for receiving a bulking device.
Figure 8:
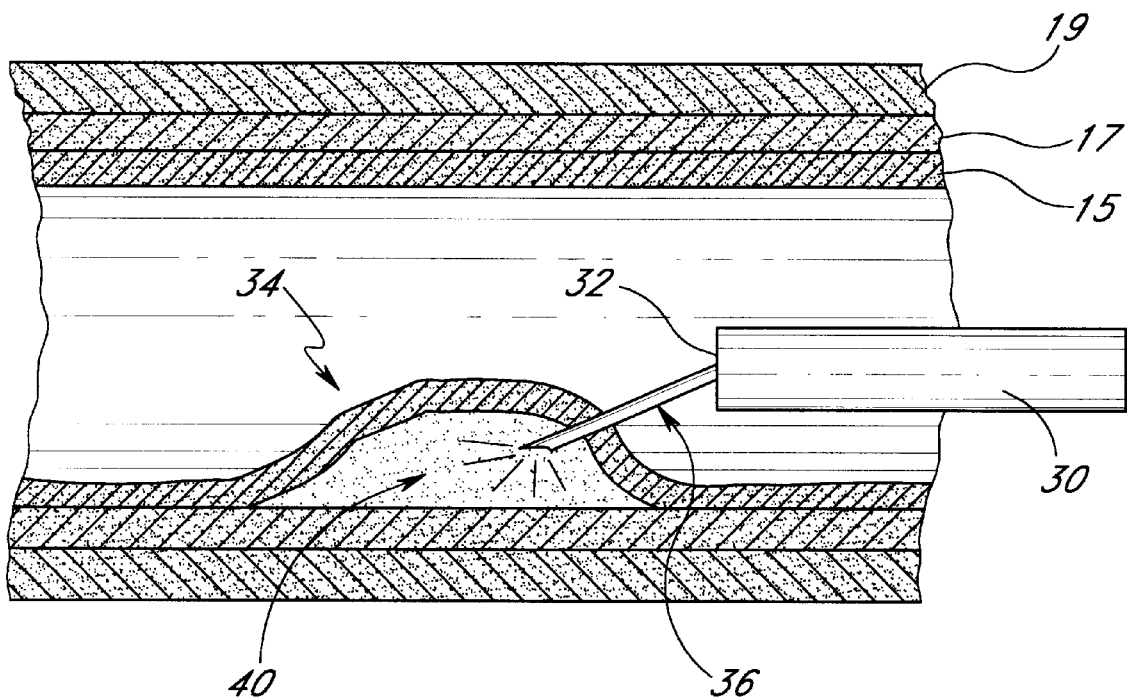
FIG. 8 is a schematic cross-sectional view of the endoscope positioned within the esophagus, forming a pocket by fluid injection.

Thus, referring to FIGS. 7 and 8, there is schematically illustrated one method of providing a blister or pocket below the mucosa. A portion of the esophagus 12 is illustrated, having a mucosa 15, submucosa 17 and circular muscle layer 19. An endoscope 30 is nasally or orally introduced and trans-esophageally advanced until a distal end 32 is positioned in the vicinity of the desired bulking device delivery site. A portion 34 of the mucosa 15 is raised into a blister, such as by introduction of a hypodermic needle 36 from the distal end 32 of endoscope 30. Hypodermic needle 36 is utilized to inject a fluid media 38 such as n-saline or other biologically acceptable material below the mucosa 15 to form a blister 40. Proper positioning of the hypodermic needle 36 can be ascertained by tactile feedback as is understood in the art. Alternatively, the portion 34 of mucosa 15 can be raised from the submucosa 17, such as by application of a vacuum to the wall of the esophagus.

Figure 9:
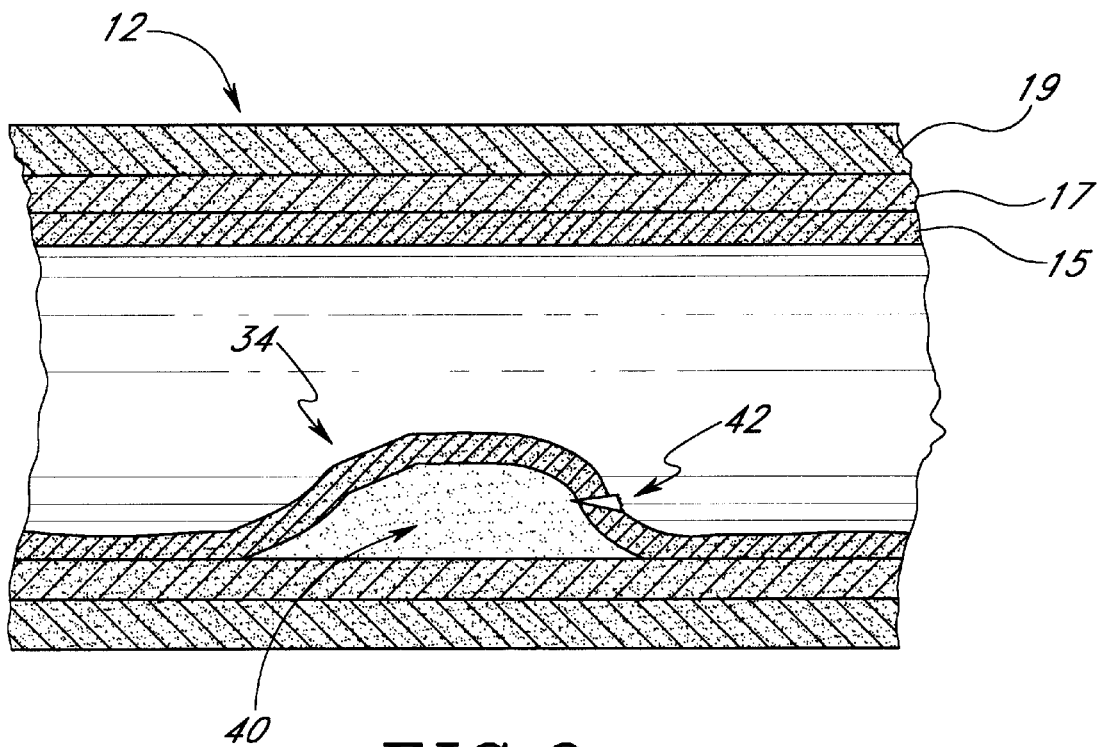
FIG. 9 is a side elevational view as in FIG. 8, illustrating an access incision.
Figure 10:
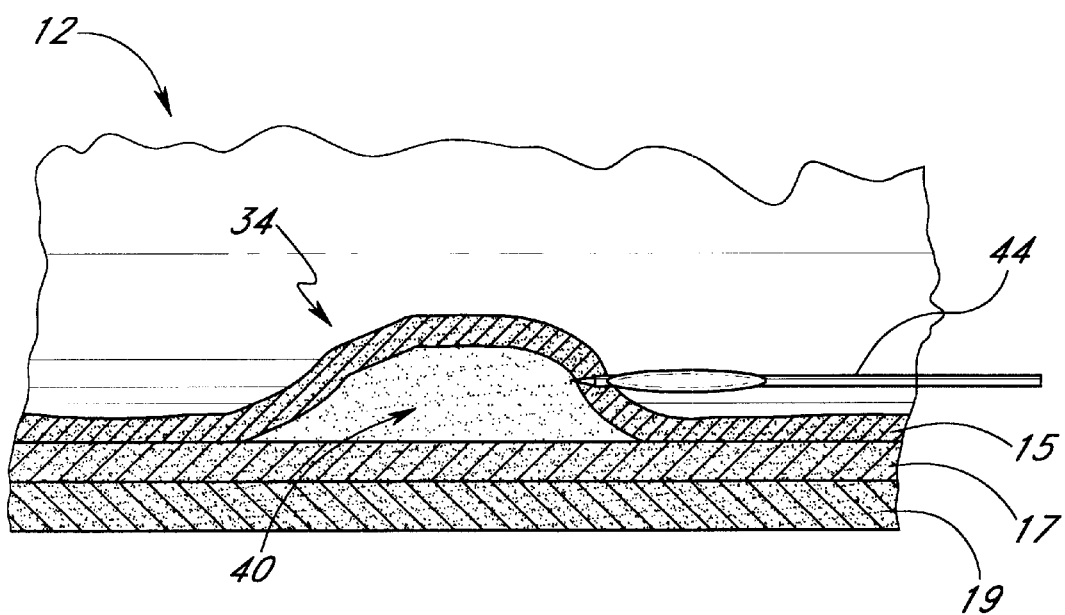
FIG. 10 is a side elevational view as in FIG. 9, illustrating a mechanical dilatation catheter during insertion into the blister.
Figure 11:
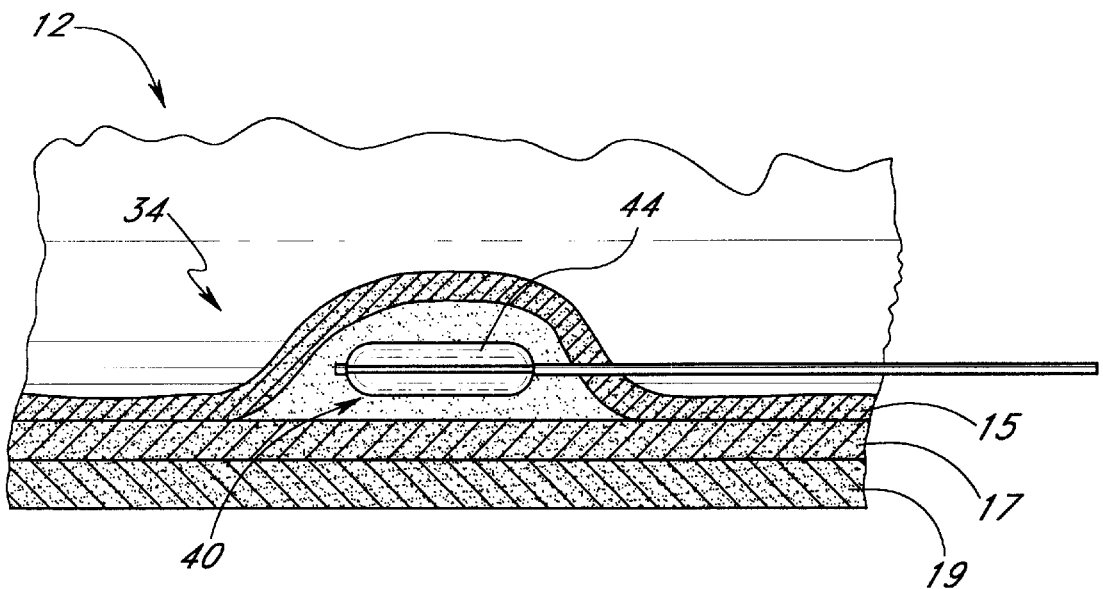
FIG. 11 is a side elevational view as in FIG. 10, with the mechanical dilatation catheter enlarged within the blister.
Figure 12:
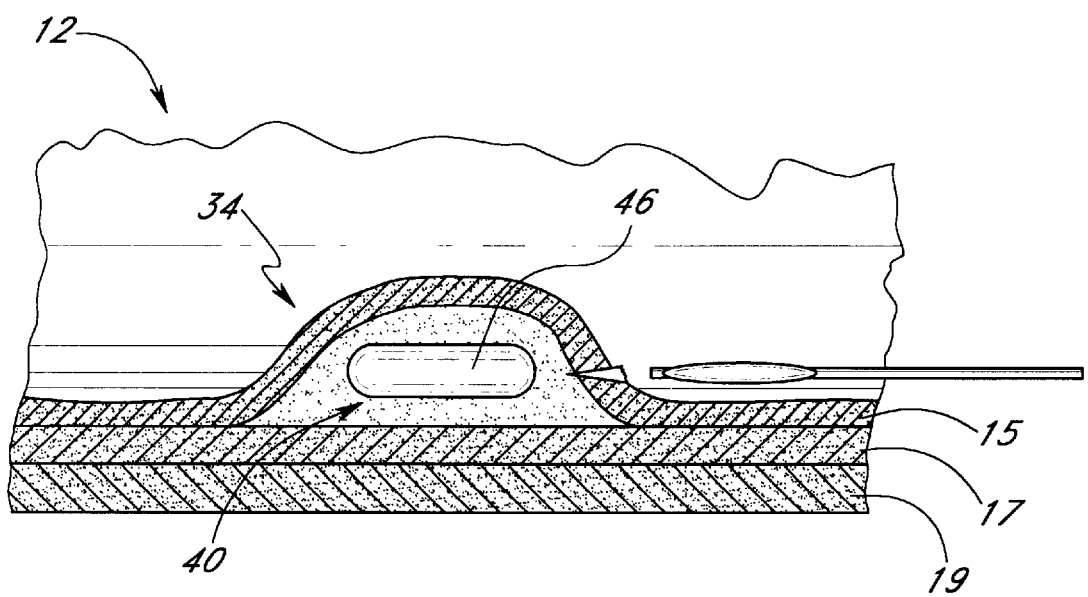
FIG. 12 is a side elevational view as in FIG. 11, illustrating the cavity formed by the dilatation catheter.

Following blister formation, a small incision or access site 42 is provided as illustrated in FIG. 9. A cavity formation device, such as a balloon dilatation catheter 44, may be introduced through the access site 42 and into the blister. The balloon 46 is inflated, thereby forming a pocket 40 within the esophagus wall. If the bulking device 16 is to be delivered within the submucosa 17, the balloon dilatation catheter 44 must generally inflate to a larger volume than the volume of the bulking device 16, due to recoil of the fibrous tissue in the submucosa 17.

Following dilatation or manipulation of another pocket forming device, the balloon dilatation catheter 44 or other device is reduced in size and removed, thereby leaving a receiving cavity 46 for one or more bulking devices 16. The bulking device 16 may then be inserted within the cavity using any of a variety of delivery implements, the specific design of which will depend upon the size and configuration of the bulking device 16. The foregoing steps may be repeated for two or more positions around the circumference of the esophagus in the vicinity of the LES, as may be desired.

Figure 13:
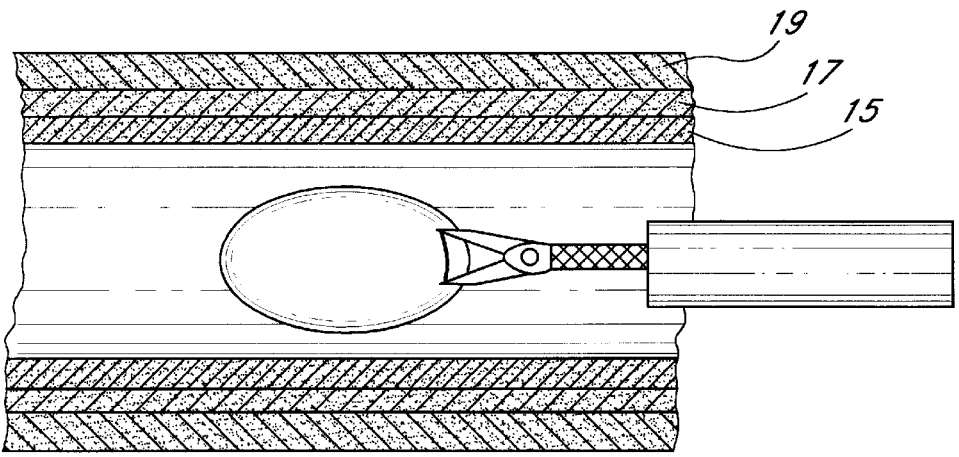
FIG. 13 is a top view of a blister, prior to forming a pocket with a cutting tool.
Figure 14:
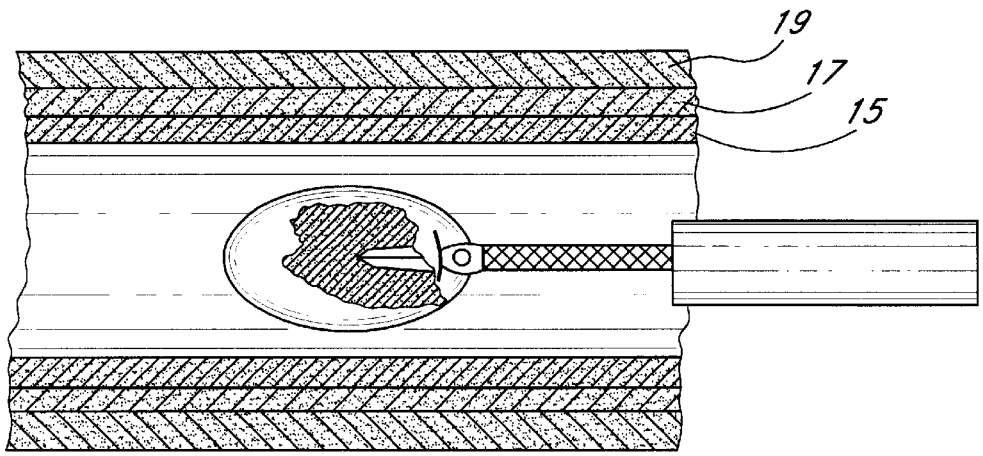
FIG. 14 is a top view as in FIG. 13, with the cutting tool inserted within the blister.
Figure 15:
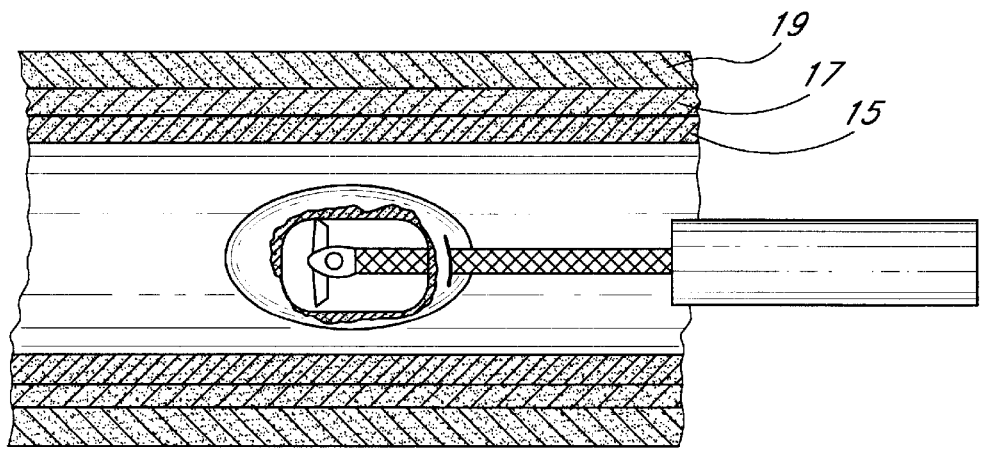
FIG. 15 is a top view of the blister as in FIG. 14, with the cutting tool cutting a pocket in the fibrous submucosa layer.

An alternate method of forming the cavity 46 is illustrated in FIGS. 13–15. In this embodiment, a mechanical cutting device, such as a scissor 48, is introduced below the mucosa 15 and manipulated to sever the springy tissue of the submucosa 12 and produce a cavity 46 for receiving the submucosal bulking device 16.

Referring to FIG. 16, there is illustrated a distal end construction for a medical device which permits reproducible access to a delivery site below a tissue surface. Notwithstanding the utility of the previously described access and delivery methods, the reproducibility of each depends upon the technical skills of the clinician. The devices illustrated in FIGS. 16–18 enhance procedure to procedure reproducibility of a submucosal prosthesis delivery, and minimize variability due to clinical experience and technical skill.

The distal end construction illustrated in FIG. 16 is in the form of a cap which may be integrally manufactured with or subsequently attached to the distal end of an endoscope or other elongate medical device. The cap 50 comprises a sidewall 52 which is generally in the form of tubular element although other constructions may be utilized. Sidewall 52 may be made from any of a variety of biocompatible metals or polymers, such as polycarbonate, acrylic, HDPE, nylon, PTFE, stainless steel, and others well known in the medical device arts. In one embodiment, the cap 50 has an axial length of about 2.2 inches, an outside diameter of about 0.6 inches, and side wall thickness of about 0.06 inches.

The sidewall 52 extends between a proximal end 54 and a distal end 56. Distal end 56 preferably blunt, to provide an atraumatic surface. The cap 50 is provided with an opening 58, preferably on the side wall 52, for receiving tissue from the target site. In one embodiment, the opening 58 has an axial length of about 1.25 inches, and a width of about 0.28 inches. In this embodiment, a generally rectangular opening 58 is provided to facilitate introduction of an elongate bulking element into the target site. Other configurations for first opening 58 may be utilized, as is discussed below, depending upon the size and shape of the prosthesis.

A tissue stabilizing or limit surface 62 defines at least a portion of the wall of the cavity. In the illustrated embodiment, surface 62 is on the lateral face of a surface such as on a shelf or plate 60 positioned medially (towards the central longitudinal axis) from the first opening 58. Preferably, the tissue stabilizing surface 62 is provided with one or more apertures 64, which are in communication through the shelf 60 with a vacuum lumen 66 in the cap 50. Vacuum lumen 66 is adapted for coupling to a lumen in the endoscope or other medical device, so that a vacuum may be drawn on vacuum lumen 66.

The tissue stabilizing surface 62 cooperates with the tissue opening 58 to define a tissue receiving cavity 65 in the medical device. The overall shape and volume of the cavity 65 can be varied widely, depending upon the intended application. For example, tissue opening 58 can have a generally rectangular shape as in the illustrated embodiment. Alternatively, the tissue opening 58 can be in the form of an oval or ellipse, or circle, depending upon the length and width of the desired submucosal low pressure zone or prosthesis. In addition, the tissue stabilizing surface 62 can be concave in the direction of tissue opening 58 or generally planar as illustrated. In one embodiment, the tissue stabilizing surface 62 is in the form of a portion of the side wall of a cylinder, such that it has a substantially linear configuration in the axial direction and a radiused curve in the transverse cross-section. Generally conical or hemispherical configurations for tissue stabilizing surface 62 may also be provided, with an aperture 64 at the apex thereof or a plurality of apertures 64 positioned on the tissue stabilizing surface 62. The tissue stabilizing surface 62 may also be provided with friction enhancing structures, such as a plurality of ridges or grooves to minimize sliding of the submucosal tissue along the surface 62.

In use, tissue which is positioned adjacent the tissue opening 58 will be drawn into the tissue opening 58 and adjacent the tissue stabilizing surface 62 in response to application of vacuum through the apertures 64. The tissue stabilizing surface 62 thus acts as a limit, to reproducibly control the amount of tissue drawn into the opening 58 in response to the vacuum.

The cap 50 may be provided at its proximal end 54 with a second opening 68. Second opening 68 is adapted to be coupled to an endoscope or other medical device. For this purpose, an attachment structure 70 such as an annular recess may be provided on the proximal end 54 to facilitate insertion of the distal end of an endoscope (not shown) therein. The cap 50 may be secured to the endoscope in any of a variety of ways, such as by threaded engagement, snap fit or other interference fit structures, adhesives, or other attachment techniques which will be known in the art.

When coupled to an endoscope, a viewing lens on the endoscope is preferably oriented in the cap 50 such that tissue which has advanced into the cavity 65 can be visualized through the endoscope optics. This may be accomplished by constructing the shelf 60 from a transparent material, and/or providing a viewing aperture 72 between the lens on the endoscope and the tissue opening 58.

A working channel on the endoscope is aligned with a deployment lumen 74. Deployment lumen 74 may be defined at least in part by an internal baffle wall 76. In the illustrated embodiment, the baffle 76 is inclined radially outwardly in the distal direction to taper the inside diameter of the deployment lumen 74 in the distal direction. This assist in guiding the deployment device (discussed in greater detail below) into the tissue which has been drawn into the cavity 65. The deployment lumen 74 has a distal end 78. Deployment lumen 74 is oriented such that an elongate device which is advanced through deployment lumen 74 and out distal end 78 will extend at least partway across the tissue opening 58. A piercing device such as a needle, cautery tip or other cutting structure which is advanced through deployment lumen 74 will enter and travel beneath tissue which is brought into contact with tissue stabilizing surface 62.

Figure 17A:
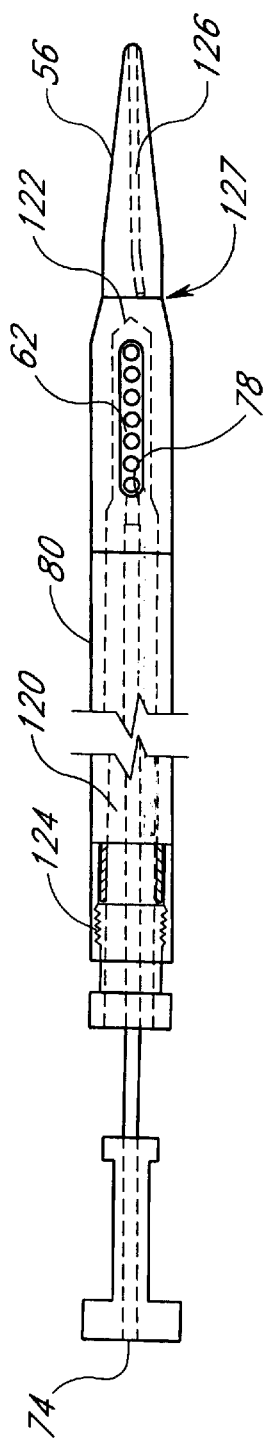
FIG. 17A is a bottom view of the overtube illustrated in FIG. 17.

Referring to FIGS. 17 and 17A, there is illustrated a side elevational view of an overtube embodiment adapted to be advanced over the distal end of an endoscope and pulled proximally like a sheath to adapt the endoscope for the present application. In an alternate application, discussed in connection with FIG. 18, infra, the distal end configuration is on an access catheter without an associated endoscope.

In the illustrated embodiment, a flexible tubular sheath 80 extends proximally from the distal end assembly 56. Tubular sheath 80 is preferably dimensioned to receive and closely fit a standard endoscope. For example, one common endoscope for use in the present invention has an outside diameter of about 9.8 mm. The corresponding lumen 120 in tubular sheath 80 has an inside diameter of about 11 mm and an axial length within the range of from about 60 cm to about 120 cm. Tubular sheath 80 may comprise any of a variety of polymeric materials which are conventional in the catheter manufacturing arts. The tubular sheath 80 may be integrally formed with or bonded to the side wall 53 of midsection 53 and other structural components of the distal end 56 assembly. In one embodiment, tubular sheath 80 comprises PVC, having a wall thickness of about 0.050".

A proximally extending deployment lumen 74 is defined within a tubular wall 82. In this construction, the tubular wall 82 extends in parallel with at least a portion of the endoscope, so that the deployment catheter or other deployment device need not be advanced through a working channel in the endoscope. The deployment lumen 74 terminates in a distal end 78 which directs the deployment device or piercing device into tissue which has been drawn into the cavity 65. Proximally, the deployment lumen 74 may terminate in a manifold, which may additionally be provided with a flush port 128 if desired.

The central lumen 120 for receiving an endoscope extends between a distal end 122 in midsection 53 and a proximal endoscope seal 124. A distal tip 56 preferably extends beyond the midsection 53, to permit atraumatic introduction of the device. Distal tip 56 is preferably provided with a guidewire lumen 126, to facilitate over the wire placement. Guidewire lumen 126 can extend proximally throughout the length of the device, or exit at a proximal side port 127 along the side of the device such as at about the proximal end of the distal tip 56 section.

In one embodiment of the overtube illustrated in FIG. 17, the tubular sheath 80 and distal end 56 assembly have an overall length on the order of about 34.8". The outside diameter of the overtube is about 0.7", and the depth of the tissue cavity between the tissue opening 58 and tissue stabilizing surface 62 is about 0.2". Any of these dimensions may be varied, to accommodate different functional characteristics and other clinical objectives of the device, as will be apparent to those of skill in the art in view of the disclosure herein.

Figure 18:
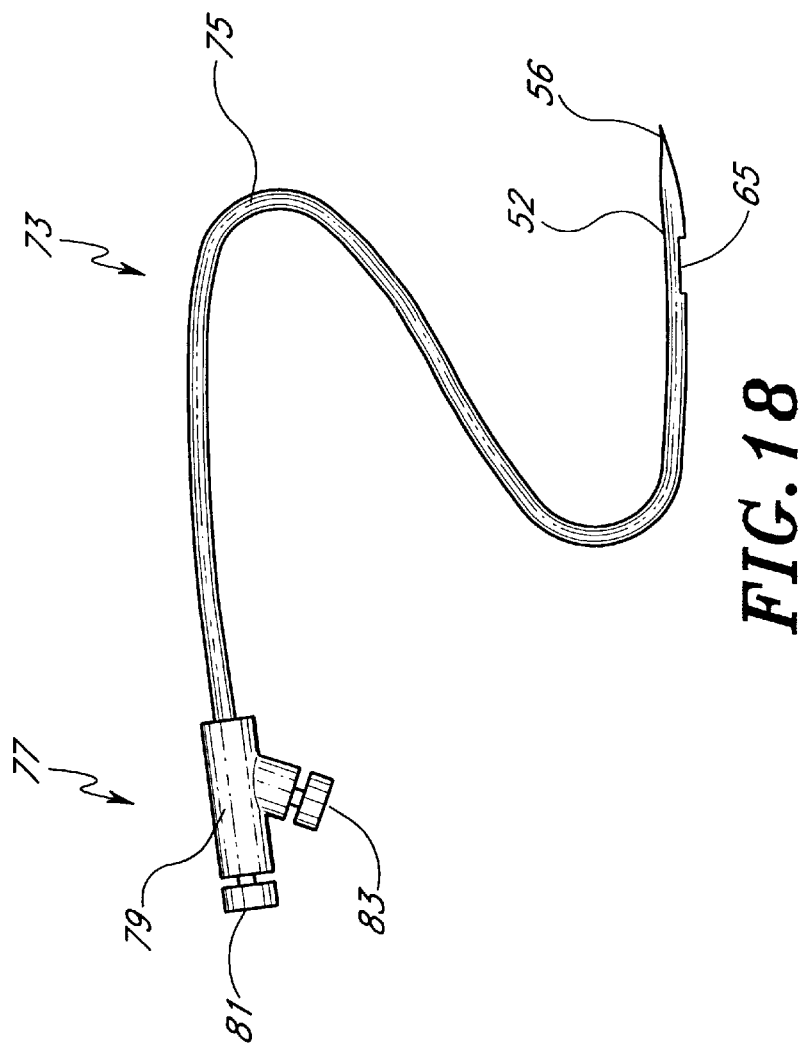
FIG. 18 is a side elevational schematic view of a bulking device deployment catheter, such as for "blind" deployment.

Referring to FIG. 18, there is illustrated a side elevational schematic view of a "blind" embodiment of the submucosal delivery device in accordance with the present invention. The delivery device 73 is provided with an elongate flexible body 75, having a proximal end 77 and a distal end 56. Proximal end 77 is provided with a manifold 79 which may have any of a variety of features depending upon the functionality of the device. In the illustrated embodiment, the manifold 79 is provided with a deployment device access port 81. Access port 81 is in communication with a deployment lumen 74. Deployment lumen 74 extends throughout the length of flexible body 75, and communicates with a distal end 78 at or near the tissue cavity 65 as has been discussed.

The proximal manifold 79 is further provided with a vacuum port 83. Vacuum port 83 is in communication with a vacuum lumen (not illustrated) extending throughout the length of flexible body 75, and communicating with the tissue cavity 65 through one or more apertures 64 as has been discussed.

The embodiment of the delivery device illustrated in FIG. 18 may be utilized without direct visualization. A sensor is preferably included to indicate to the clinician when sufficient tissue has been drawn into the cavity 65. Any of a variety of sensors may be devised for this purpose. In one embodiment, a pressure sensor is placed in communication with the vacuum lumen. When sufficient tissue has entered the cavity 65 to occlude the one or more vacuum ports 83, a change in pressure will be perceivable in the vacuum lumen. Any one or combination of visual, audible, or tactile feedback can be provided to a clinician, indicating that a sufficient volume of tissue has entered the cavity 65. Alternatively, any of a variety of physical pressure gages can be provided in the cavity, and utilized to detect the presence of tissue therein.

The deployment catheter 73 may be used in any of a variety of ways, and dimensions and materials may be modified to accommodate the specific intended use. For example, the deployment device 73 can be utilized to access a treatment site in the esophagus through either the nose or the mouth. Particularly in an application intended to be advanced through the nose, the distal end 56 is provided with an elongate tapered atraumatic tip to enable the device to deflect off the soft palate with minimal trauma. Distal tips having an axial length within the range of from about 1" to about 5" are contemplated, and may be constructed (e.g., molded) from polyurethane or other soft material.

For either nasal or oral access, the tubular body 75 may have a diameter of within the range of from about 5 mm to about 20 mm, and an axial length within the range of from about 70 cm to about 120 cm. Tubular body 75 may be constructed in any of a variety of manners well known in the catheter construction arts. For example, much of the length of tubular body 75 may comprise a two lumen extrusion with additional lumen (e.g. a guidewire lumen) being provided if additional functionalities are desired. The extrusion may comprise any of a variety of materials such as HDPE, PTFE, nylon, acrylic, PVC and other polymers which are well known in the art. The distal end 56 and distal side wall 52 including the tissue cavity 65 may be separately formed and secured to the extrusion in any of a variety of ways, such as through heat melting, adhesive bonding and other techniques which are known in the art.

Figure 19:
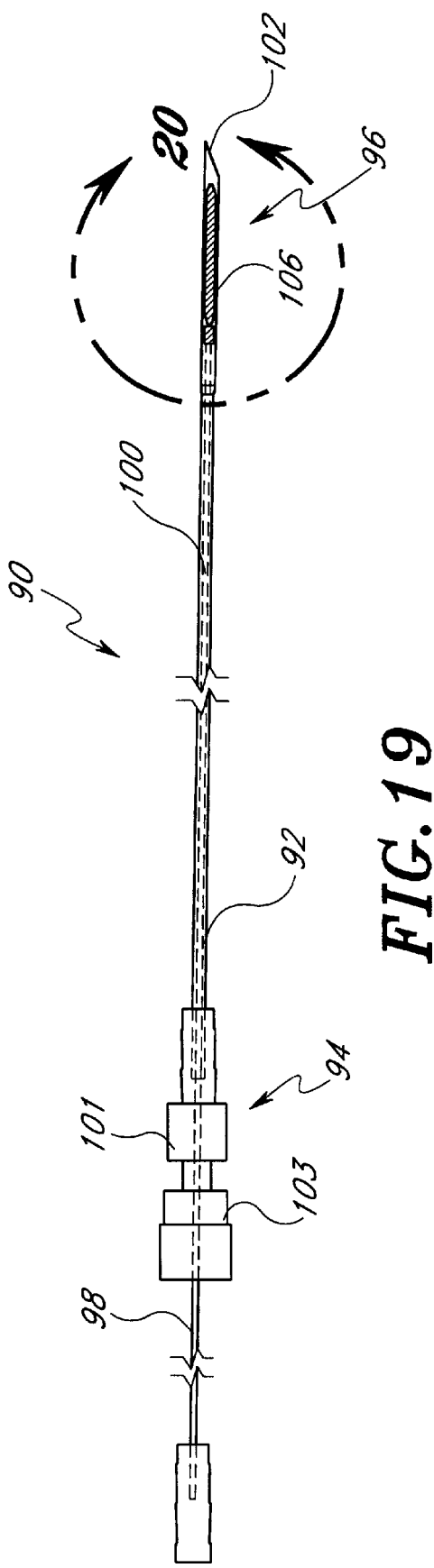
FIG. 19 is a side elevational schematic view of a prosthesis delivery needle assembly.
Figure 20:
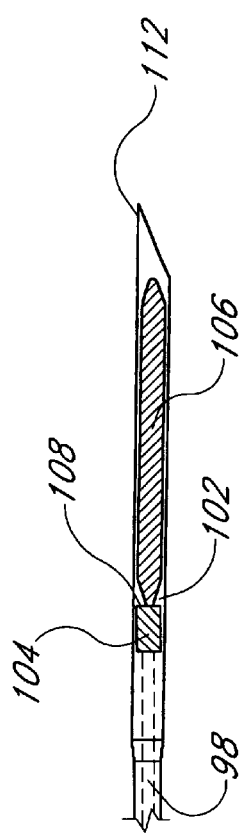
FIG. 20 is an enlarged cross-sectional view of the distal end of the delivery needle of FIG. 19.
Figure 21:
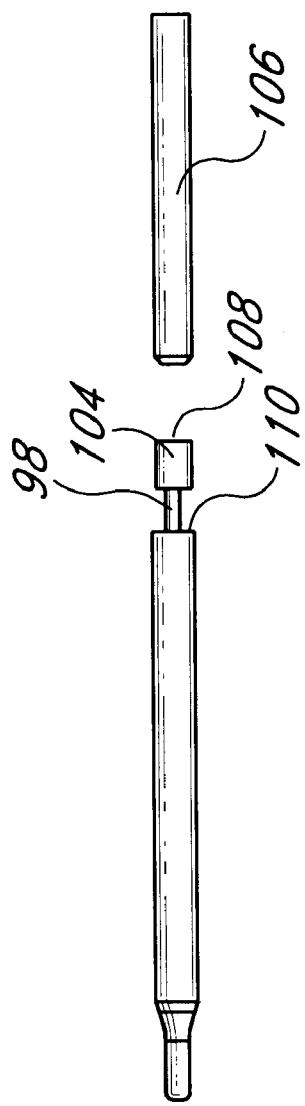
FIG. 21 is a side elevational view of the distal end shown in FIG. 20, with the plunger distended to eject a bulking element.

Referring to FIGS. 19 through 23, there are illustrated a variety of deployment devices which may be advanced through the deployment lumen 74 of any of the embodiments previously described. Referring to FIG. 19, a deployment device 90 generally comprises an elongate flexible body 92 having a proximal end 94 and a distal end 96. An inner element 98 is axially movably positioned within an outer tube 100. A proximal locking mechanism 101 is provided on a proximal control 103. At the distal end 96, the outer tube 100 comprises a cavity 102 for receiving bulking media 106. A plunger 104 having a distal surface 108 is provided on the distal end of the inner element 98, and is axially movably positionable within the cavity 102. As illustrated in FIG. 21, distal advancement of the inner element 98 causes the plunger 104 to distally deploy the bulking media 106.

The deployment device 90 may be constructed in any of a variety of ways which are known in the catheter construction arts. For example, either or both of the inner element 98 and outer tube 100 may be metal tubes such as hypotubes, dimensioned such that the inner element 98 is axially moveable within the outer tube 100. Alternatively, either or both of the inner element 98 and outer tube 100 may be polymeric extrusions. The inner element 98 may either be a tubular structure or a solid rod.

In an embodiment intended to advance through a deployment lumen 74 having an inside diameter of about 0.100", the outer tube 100 has an outside diameter of no more than about 0.095". In one embodiment, the inner element 98 comprises a stainless steel rod, and the outer tube 100 comprises polyimide tube. The deployment device 90 has an axial length within the range of from about 70 cm to about 100 cm, and, in the illustrated embodiment, about 100 cm.

Preferably, the length of axial travel of the inner element 98 with respect to the outer tube 100 is sufficient to advance the distal pushing surface 108 to a position beyond the distal end 110 of the cavity 102. In an embodiment intended to deliver a hydrogel bulking device having (an unexpanded) diameter of about 2 mm and axial length of about 20 mm the deployment device 90 is constructed to permit the distal pushing surface 108 on plunger 104 to extend at least about 10 mm beyond the distal end 110 of the cavity 102. The present inventors have determined that permitting the plunger to extend beyond the distal end of the cavity 102 permits the deployment of semi-liquid or gel form bulking agents into a submucosal tissue tract while minimizing the likelihood that trailing threads of the bulking agent will extend proximally through the tissue access pathway upon proximal retraction of the deployment device 90.

In one embodiment, the distal end 96 is provided with a sharpened point 112 for piecing a tissue surface. In this embodiment, an outer protective sheath may be axially moveably carried on the outer tube 100, such that distal advancement of the outer cover 114 will shield the distal pointed tip 112. In an alternative embodiment (FIG. 21), the distal end 96 is blunt.

The deployment or delivery systems disclosed in FIGS. 19 through 22, among other deployment devices, can be used in accordance with the present invention to deliver any of a wide variety of expandable bulking devices or other submucosal prostheses. Suitable bulking devices fall into either of two broad categories. The first are bulking devices which inherently expand to achieve a predetermined configuration. This category includes a wide variety of capsules, foams and hydrogels as have been disclosed previously herein. The second category includes fluids or gels which do not inherently assume any particular shape upon expansion or solidification, but which are able to achieve a predetermined shape in situ when used in accordance with the present invention.

Concerning the first category, a variety of capsules and foams have already been disclosed herein. In addition, a variety of hydrogels may be used such as those disclosed in U.S. Pat. No. 4,943,618 issued Jul. 24, 1990 to Stoy et al., entitled Method for Preparing Polyacrylonitrile Copolymers by Heterogeneous Reaction of Polyacrylonitril Aquagel, and U.S. Pat. No. 5,252,692 issued Oct. 12, 1993 to Lovy et al. entitled Hydrophilic Acrylic Copolymers and Method of Preparation, the disclosures of both of which are incorporated in their entireties herein by reference. Preferably, a hydrogel or other material will be selected which has an expansion ratio on the order of at least about 100% and preferably in excess of 500%, particularly in the transverse direction. Thus, a hydrogel rod having a diameter of about 1 mm when positioned within the cavity 102 will preferably expand to a cross section of about 5 or 6 millimeters or greater in situ. Preferably, the hydrogel or other bulking media will exhibit a sufficient expansion rate that it will expand sufficiently to lock in place before migrating from the deployment site such as through the introduction tissue tract.

Another aspect of the present invention is the ability to introduce a bulking media in a fluid or gel form which possess no inherent ability to achieve a predetermined shape, yet, when used with the devices of the present invention, will produce a bulking structure having a predetermined configuration. This is achieved through the interaction between the devices disclosed herein and the anatomy of the esophagus.

The central esophageal lumen is surrounded by a mucosa layer having a thickness on the order of from about 1.0 to about 2.0 mm. Below the mucosa is the submucosa, having a thickness on the order of about 0.5 to about 1 mm. Below the submucosa is a muscle layer having a variable thickness, generally on the order of about 2 mm to about 3 mm. When mucosa is drawn into the cavity on the delivery device of the present invention, a reproducible low pressure region is created in the submucosa which corresponds in shape to the shape of the mucosa which has been drawn into the cavity. The delivery channel directs a deployment needle or other device through the mucosa and directly into the low pressure region of the submucosa. Thus, in accordance with the present invention, a polymerizable or otherwise hardenable fluid or gel may be injected into the low pressure zone in the submucosa at the target site, and that fluid or gel will assume a shape which is strongly influenced by the shape of the opening 58 and depth of the cavity 65. In addition, the muscle layer is substantially unaffected by the application of vacuum to the mucosa using the devices disclosed herein, because the deployment lumen directs the deployment device generally in parallel to the muscle layer. This minimizes the risk of piercing the muscle layer beneath the submucosa. Among other complications from piercing the muscle layer, the aorta and vagus nerve are positioned closely outside of that layer.

Any of a variety of fluids or gels may be utilized, such as UV curable materials, heat or catalytically initiated polymerizable materials, and others which can be optimized through routine experimentation by those of ordinary skill in the art in view of the disclosure here. Another useful class of bulking media includes biocompatible polymers which are soluble in a biocompatible solvent but insoluble in the submucosal tissue. The biocompatible solvent is soluble or dispersible in the tissue, such that the biocompatible solvent diffuses away from the biocompatible polymer in situ, thereby permitting the biocompatible polymer to precipitate, polymerize, or otherwise harden into a bulking mass. In one embodiment, the bulking media further includes a contrast agent, to permit visualization of the bulking mass during and following implantation of the bulking media. Examples of suitable bulking media are disclosed in U.S. Pat. No. 5,785, 642, issued Jul. 28, 1998 to Wallace et al., entitled Methods for Treating Urinary Incontinence in Mammals, the disclosure of which is incorporated in its entirety herein by reference.

Figure 22:
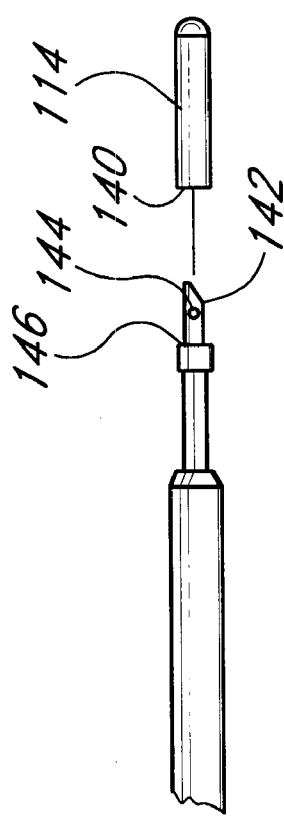
FIG. 22 is a side elevational view of an alternate distal end of a deployment catheter, adapted to deploy an inflatable balloon.

Referring to FIG. 22, there is disclosed an alternate distal end 96 for the deployment device 90, adapted to deploy an inflatable balloon 114. The balloon 114 is provided with an opening 140 on a proximal end thereof, which includes a pierceable septum or other sealable closing structure (not illustrated). A tube 142 having at least one inflation aperture 144 thereon is moveably carried within the closure structure during insertion of the deployment device 90. Proximal travel of balloon 114 along the inflation tube 142 is limited by a stop 146. Following placement within a submucosal cavity, the balloon 114 is inflated and inflation tube 142 is proximally withdrawn thereby leaving the inflated balloon in place. Deflation of the balloon is prevented by closure of the pierceable septum. The balloon may be deployed by advancing the delivery system into the submucosal space, retracting covering sheath 147 to expose the balloon 114, inflating the balloon 114 through inflation tube 142 and withdrawing the catheter system leaving the balloon in place.

Although the foregoing invention has been disclosed in terms of certain preferred embodiments, other specific embodiments can be constructed in view of the disclosure herein without departing from the spirit of the scope of the present invention. Accordingly, the scope of the Applicant's invention is to be determined by reference to the attached claims, which are not limited to any of the particular embodiments disclosed herein.

What is claimed is:

1. An overtube for receiving an endoscope, comprising:
   an elongate, flexible tubular body, having a proximal end and a distal end and a longitudinal axis;
   at least one lumen extending therethrough for receiving an endoscope;
   an opening on the body, in communication with the lumen; and
   a limit surface within the body, aligned with the opening, for limiting the depth to which tissue can enter the opening.

2. An overtube as in claim 1, wherein the tubular body has a sidewall, and the opening is in the sidewall.

3. An overtube as in claim 2, wherein the limit surface lies on a first plane which is substantially parallel to the longitudinal axis.

4. An overtube as in claim 3, wherein the limit surface cooperates with the opening to form a tissue cavity, and the tissue cavity has a depth in the radial direction within the range of from about 10% to about 90% of the outside diameter of the body.

5. An overtube as in claim 4, wherein the depth is within the range of from about 20% to about 50% of the outside diameter.

6. An overtube as in claim 1, wherein the limit surface comprises a plurality of apertures.

7. An overtube as in claim 1, wherein the opening has an axial length and a circumferential length, and the axial length is within the range of from about 5 mm to about 50 mm.

8. An overtube as in claim 7, wherein the circumferential length is within the range of from about 2 mm to about 10 mm.

9. A method of introducing a flowable media into a predetermined shape beneath a tissue layer, comprising the steps of:
   identifying a first site on a tissue surface;
   lifting tissue a predetermined distance away from a plane of the surface to create a low pressure zone beneath the tissue;
   injecting a first volume of flowable media into the low pressure zone so that the media takes on a shape which is influenced by the low pressure zone; and
   permitting the media to harden sufficiently to substantially retain the shape.

10. A method of introducing a flowable media as in claim 9, wherein the identifying a site on a tissue surface step comprises identifying a site on the wall of the esophagus.

11. A method of introducing a flowable media as in claim 10, wherein the site is adjacent the lower esophageal sphincter.

12. A method of introducing a flowable media as in claim 9, further comprising the step of identifying a second site and introducing a second volume of flowable media into the second site.

13. A method of introducing a flowable media as in claim 9, wherein the flowable media comprises a hydrogel material.

14. A method of introducing a flowable media as in claim 9, wherein the permitting step comprises initiating polymerization of the flowable media.

15. A method of introducing a flowable media as in claim 9, wherein the lifting step comprises lifting a predetermined volume of tissue by drawing the tissue into a cavity on a medical device under vacuum.

16. A method of introducing a flowable media as in claim 12, wherein the first site is circumferentially offset from the second site.

17. A method of introducing a flowable media as in claim 9, wherein the site is on the posterior wall of the esophagus.

18. A method of introducing a flowable media as in claim 9, wherein the injecting step comprises injecting the media into the submucosa.

19. A method of introducing a flowable media as in claim 9, wherein the injecting step comprises injecting the media beneath the mucosa.

20. A method of stabilizing a tissue site and introducing a prosthesis beneath the tissue, comprising the steps of:
   providing an elongate, flexible, tubular device, having a side opening near a distal end thereof;
   positioning the side opening at the site;
   applying suction to the device to draw tissue laterally into the side opening;
   limiting lateral advance of the tissue into the device by contacting the tissue with a limiting surface within the device; and
   introducing a prosthesis beneath the surface at the site while the tissue is in contact with the limiting surface.

21. A method as in claim 20, wherein the positioning step comprises introducing the device into the esophagus through the nose.

22. A method as in claim 20, wherein the positioning step comprises introducing the device into the esophagus through the mouth.

23. A method as in claim 20, wherein the introducing a prosthesis step comprises introducing a hydrogel.

24. A method as in claim 20, wherein the introducing a prosthesis step comprises introducing a polymer and a solvent.

25. A method as in claim 20, wherein the introducing a prosthesis step comprises introducing a hardenable media.

26. A method as in claim 25, further comprising the step of hardening the media by application of UV light.

27. A method as in claim 25, further comprising the step of hardening the media by permitting a solvent to dissipate from the media.

28. A method as in claim 25, further comprising the step of hardening the media by permitting the media to polymerize.

29. A method as in claim 25, further comprising the step of permitting the media to expand at the site.

30. A delivery system for delivering a bulking component beneath the surface at a treatment site, comprising:

first elongate body having a proximal end, a distal end, and a tissue stabilizer near the distal end; and a second elongate body movably associated with the first elongate body and carrying a deployable bulking component into tissue stabilized by the tissue stabilizer.

31. A delivery system as in claim 30, wherein the tissue stabilizer comprises a cavity on the first body.

32. A cap for attachment to an endoscope to produce a submucosal delivery device, comprising:

a tubular body, having a side wall, a proximal end and a distal end;

a first opening in the side wall;

a shelf in the body, spaced radially inwardly from the first opening; and a second opening on the proximal end of the body, for connection to the endoscope.

33. A method of introducing a prosthesis beneath a tissue surface, comprising the steps of:

providing a delivery device having an elongate body with a proximal end and a distal end, a concavity near the distal end and a prosthesis introduction lumen having a distal opening directed across the concavity;

positioning the concavity adjacent a site on a tissue surface;

drawing tissue into the concavity; and advancing a prosthesis out of the distal end of the delivery lumen and through the tissue surface.

34. A delivery device for introducing a prosthesis beneath a tissue surface, comprising:

an elongate body, having a proximal end and a distal end;

a tissue stabilizing surface on the body; and a deployment lumen extending through the body, the deployment lumen having a longitudinal axis and a distal end;

wherein the distal end of the deployment lumen is positioned proximally of the tissue stabilizing surface.

35. A delivery device for introducing a prosthesis beneath a tissue surface as in claim 34, wherein the tissue stabilizing comprises a concave surface.

36. A delivery device for introducing a prosthesis beneath a tissue surface as in claim 34, further comprising a suction lumen extending through the body and communicating with the tissue stabilizing surface.

37. A delivery system for delivering an expandable submucosal bulking agent, comprising:

an elongate flexible body having a proximal end, a distal end and a tissue stabilizer near the distal end;

a tubular cannula, having a sharpened distal end, positioned within the body, the cannula axially movable such that the sharpened distal end can penetrate tissue stabilized by the stabilizer; and a plunger movably positioned within the cannula for ejecting a bulking agent positioned within the cannula;

wherein the plunger is distally advanceable beyond the distal end of the sharpened tip.

38. A delivery system as in claim 37, wherein the tissue stabilizer comprises a cavity on the side of the flexible body.

39. A delivery system as in claim 38, wherein the tubular body further comprises a lumen in communication with the cavity for applying vacuum to the cavity.

* * * * *